United States Patent [19]

Fayngold

[11] Patent Number: 5,120,320
[45] Date of Patent: Jun. 9, 1992

[54] I.V. INFUSION OR BLOOD COLLECTION ASSEMBLY WITH AUTOMATIC SAFETY FEATURE

[75] Inventor: Zevulen Fayngold, Livingston, N.J.

[73] Assignee: Becton, Dickinson and Company, Franklin Lakes, N.J.

[21] Appl. No.: 654,846

[22] Filed: Feb. 13, 1991

[51] Int. Cl.⁵ .................................. A61M 5/32
[52] U.S. Cl. ........................... 604/177; 604/174; 604/263
[58] Field of Search ............... 604/162, 177, 198, 174, 604/93, 158, 164, 171, 263, 192

[56] References Cited

U.S. PATENT DOCUMENTS

| | | | |
|---|---|---|---|
| 3,572,334 | 3/1971 | Petterson | 604/162 X |
| 4,140,108 | 2/1979 | Nugent | 128/2 F |
| 4,160,450 | 7/1979 | Doherty | 128/214.4 |
| 4,170,993 | 10/1979 | Alvarez | 128/214 |
| 4,676,783 | 6/1987 | Jagger et al. | 604/171 |
| 4,781,692 | 11/1988 | Jagger et al. | 604/164 |
| 4,820,282 | 4/1989 | Hogan | 604/177 X |
| 4,834,708 | 5/1989 | Pillari | 604/165 |
| 4,846,808 | 7/1989 | Haber et al. | 604/195 |
| 4,888,001 | 12/1989 | Schoenberg | 604/162 |
| 4,917,669 | 3/1990 | Bonaldo | 604/198 X |
| 4,935,011 | 6/1990 | Hogan | 604/177 |
| 4,941,881 | 7/1990 | Masters et al. | 604/162 |
| 4,943,283 | 7/1990 | Hogan | 604/198 |
| 4,969,876 | 11/1990 | Patterson | 604/171 |

Primary Examiner—John J. Wilson
Assistant Examiner—Jeffrey A. Smith
Attorney, Agent, or Firm—Robert P. Grindle

[57] ABSTRACT

An intravenous infusion set and/or blood collection assembly is provided with a safety feature for covering the used needle with a simple movement. The assembly is comprised of a structure which is of very economical and simple construction, which allows for manual mounting, if required, but which may be formed and handled on a mass production line for rapid production, as required. The safety feature is a two-part shield which when placed in cooperating relationship, allows accommodation of a conventional unmodified blood collection needle and body including the usual handling wings. After use, the body with the needle are pulled rearwardly so that the wings do not need to be touched but moved through slots past an abutment into positive locking slots which prevent the body, wings and needle from moving out of the shield thereafter. The two-part shield may be connected by a living hinge and is comprised of a semi-rigid thermoplastic material which gives for passage of the needle body and wings from the use position to the locked position.

7 Claims, 5 Drawing Sheets

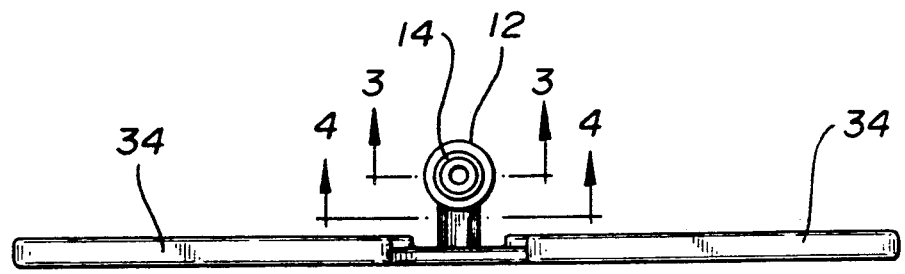
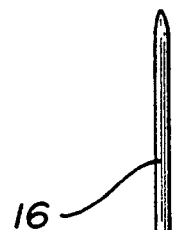
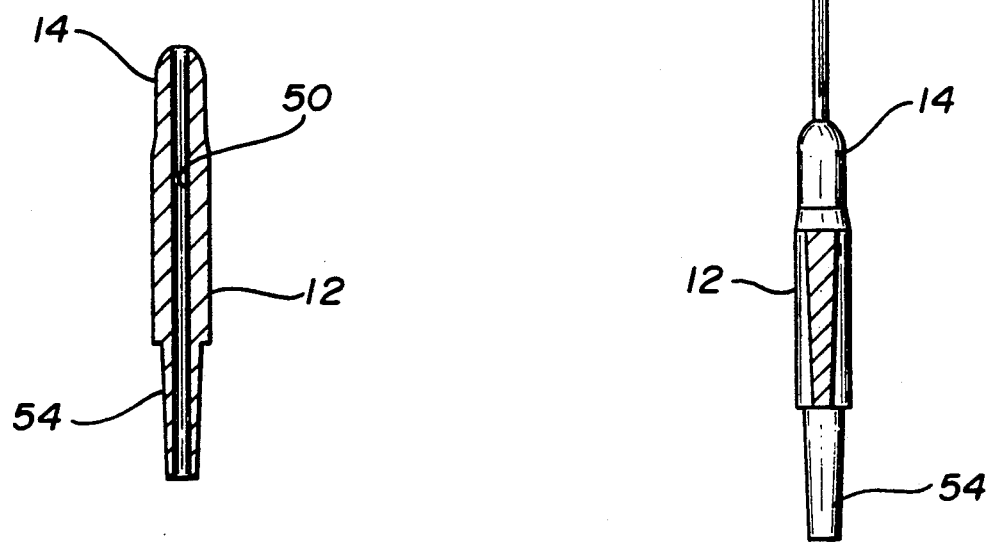

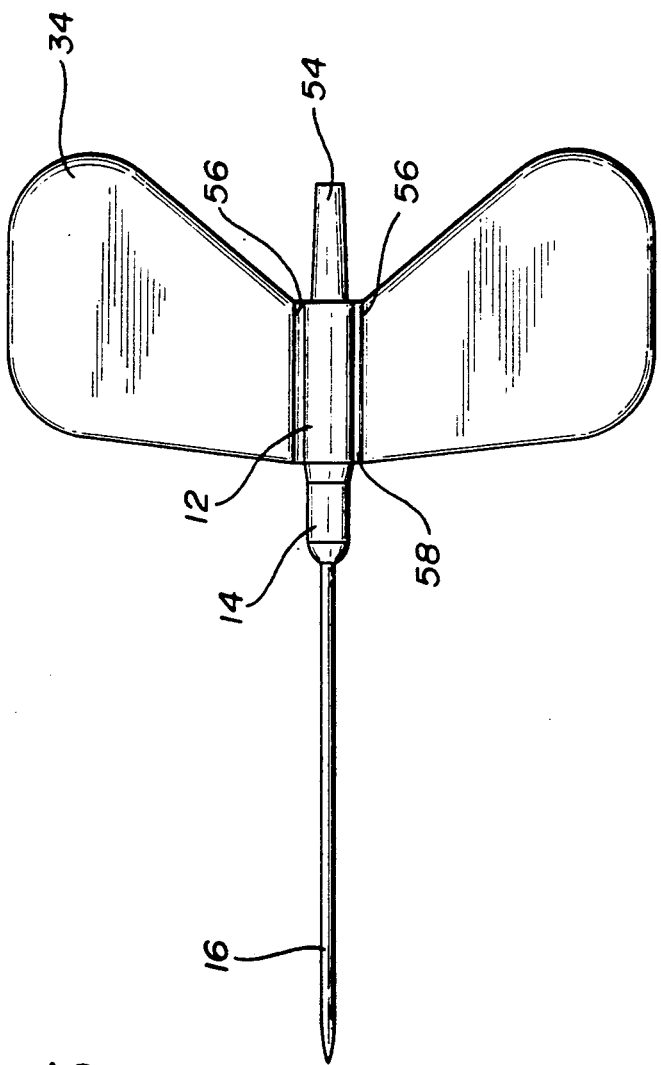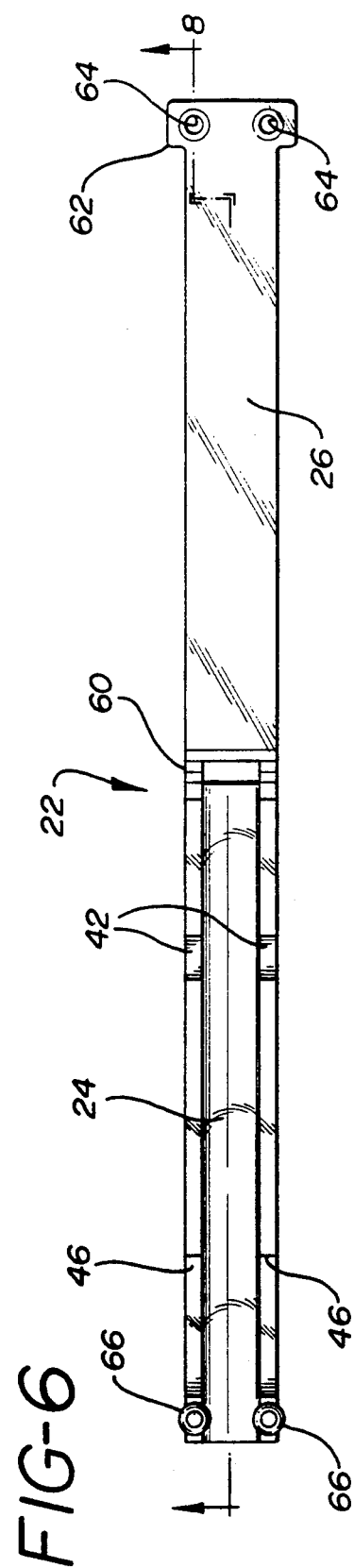

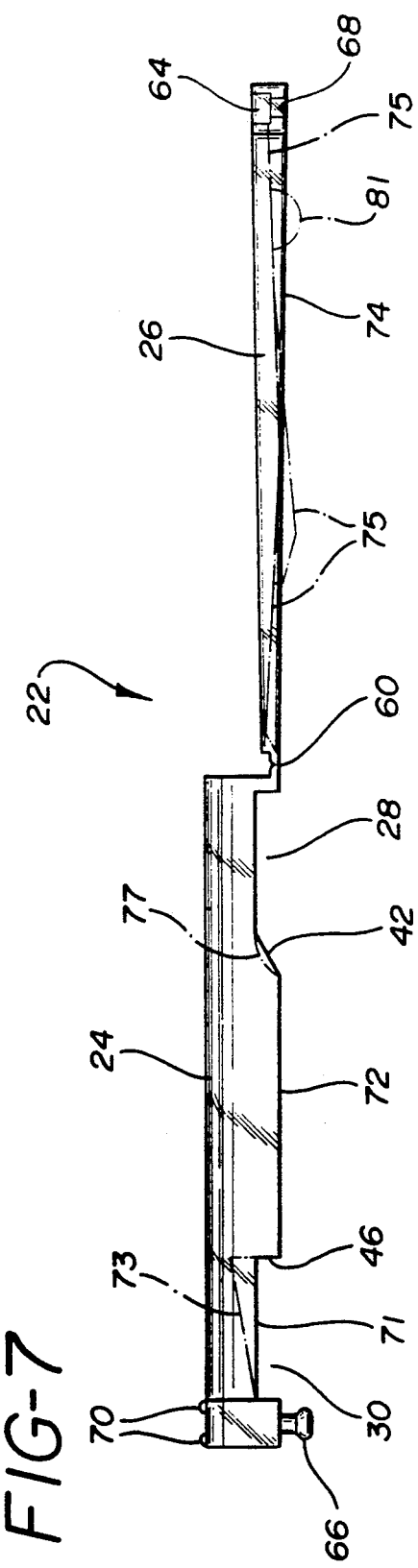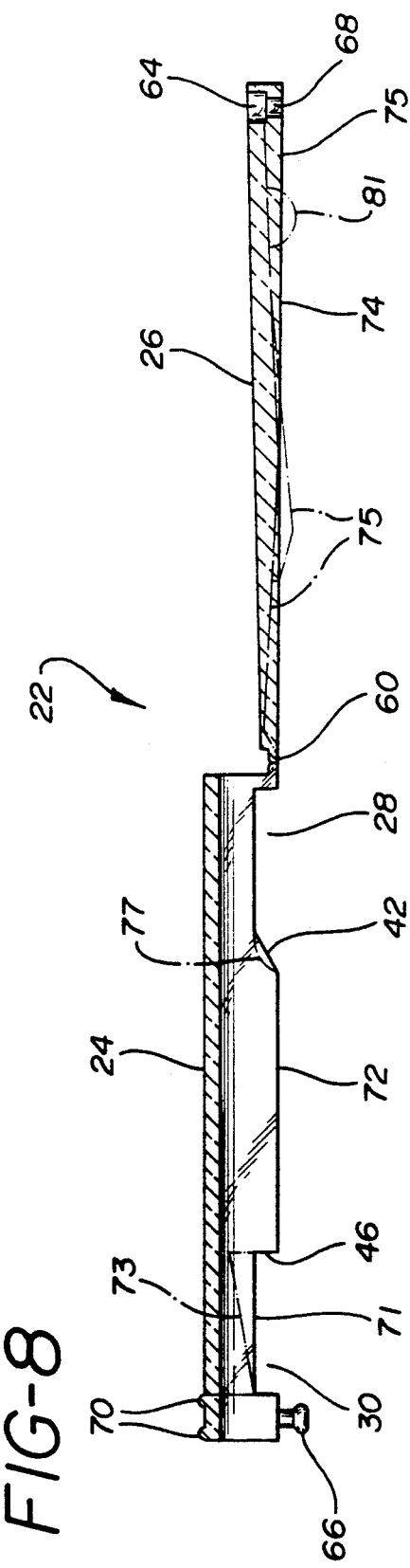

I.V. INFUSION OR BLOOD COLLECTION ASSEMBLY WITH AUTOMATIC SAFETY FEATURE

BACKGROUND AND DESCRIPTION OF THE INVENTION

The present invention relates to a conventional I.V. infusion set or blood collection assembly. Such an assembly includes an elongated small gauge plastic flexible tubing material having at one end thereof a needle and a body for holding the needle. Usually, the needle body is adhered to the one end of the flexible tube by friction. At any rate, the needle body includes wings extending on either side for the phlebotomist or user to grasp and hold the needle body for inserting the needle into a patient. Such assemblies may be used for infusing medication into a patient or for collecting blood from a patient. Generally, at the end of the flexible tube opposite the needle body is a female luer connection for connecting supplies of fluid to be infused or for connecting some sort of apparatus for collecting blood, as required.

As everyone knows who has any connection with the medical field in the last several years, there is great concern that users of such devices as described above may be contaminated with the blood of a patient by accidental sticks of the contaminated needle. For this reason, many developments have taken place for providing some sort of covering for the contaminated needle, once it is removed from the patient. These structures usually involve some sort of shield arrangement which moves in place over the contaminated needle, once it has been removed from the patient. Representative of such arrangements include, for example, the device shown and described in U.S. Pat. No. 4,170,993, which is a fairly early structure utilizing a rather involved locking slot arrangement for moving the contaminated needle into a covered position.

Two fairly simple structures for retracting a contaminated needle into a sleeve protection arrangement include, for example, U.S. Pat. Nos. 4,676,783 and 4,781,692 both of which utilize a friction engagement structure for holding the covering shield over the contaminated needle. However, it has been found that neither one of these structures provide a positive locking arrangement for insuring that the needle does not become uncovered. That is, the frictional engagement is not positive enough in many instances to prevent accidental slippage of the needle out of the shield under certain circumstances in a hospital environment, for example.

A fairly recent structure for covering contaminated needles includes the device shown and described in U.S. Pat. No. 4,943,283. This structure does not accommodate the usual handling wings normally utilized for blood collection, but rather a finger control structure which may not be satisfactory for some phlebotomists who wish to have the conventional wing structure for control. Other fairly recent arrangements for covering the contaminated needle in an infusion and/or blood collection assembly of the kind discussed herein, include U.S. Pat. Nos. 4,888,001 and 4,834,708. The former has a wing structure with cooperating grooves on the wings and cooperating locking abutments on the wings which allow for the wings to be folded to cover and lock over a contaminated needle. This structure is desirable in the sense that it provides a positive covering of the needle against the needle being uncovered by some unpredictable movement. However, the structure is very expensive to make for the kind of environment where many thousands of such needles are used daily. Moreover, the arrangement is somewhat unwieldy to handle during the covering procedure for covering the contaminated needle. Finally, the '708 patent mentioned above provides positive covering of the needle but includes a very involved and expensive structure for manufacture in the environment which this invention is directed.

U.S. Pat. No. 4,941,881 issued Jul. 17, 1990 includes a tube mounted I.V. infusion set with a protective sheath similar to that taught and claimed in the present application. The structure includes foldable wings which are utilized by the phlebotomist to grasp and maneuver the needle for insertion into a patient for use of the needle. When withdrawing the needle from the patient, the wings must be folded and held in place for movement in the folded position through a slot back to a locking position. While this arrangement provides positive locking of the needle inside an enclosed shield once the wings are moved to the locking position, it does require positive camming of the wings in a folded position for the rearward movement of the contaminated needle together with the associated wings from the use position to the locked position. Such maneuvering may be ponderous in the environment of removing a needle from the skin of a patient and attempting to handle the needle and the patient simultaneously.

With this invention, by contrast, an I.V. infusion and/or blood collection assembly is provided with a very inexpensive two-part semi-flexible shield assembly. The arrangement is such that the two parts may be joined together at one end with a flexible hinge, and connected at the opposite end with a fixed locking arrangement, so that the shield is closed over the needle body of a blood collection set. The arrangement is such that the cooperating parts of the shield form a forward non-locking use position for the wings and a rearward fixed locking position for moving the needle into a protected permanently locked position. The two locking positions are joined by flexible slots which allow the movement of the wings, without any flexing thereof or handling, from the use position to the locked position. Thus, the assembly provides simple rearward movement of the needle body and wings, which is the automatic movement of the contaminated needle into a shielded positively locked position for subsequent disposal.

Other objects and advantages of this invention will be apparent from the following description, the accompanying drawings and the appended claims.

DESCRIPTION OF THE DRAWINGS

FIG. 2 is a front end view of the assembly of FIG. 1 as viewed from the left hand end thereof;

FIG. 3 is a sectional view taken along lines 3—3 of FIG. 2;

FIG. 4 is a sectional view taken along lines 4—4 of FIG. 2;

FIG. 5 is a top plan view of a conventional blood infusion set needle body with associated flexible wings and needle;

FIG. 6 is a top plan view of the shield of the invention in its unfolded non-use position;

FIG. 7 is a side elevational view of the shield of FIG. 6;

FIG. 8 is a sectional view taken along lines 8—8 of FIG. 6; and

DETAILED DESCRIPTION OF THE INVENTION

Figure 1:
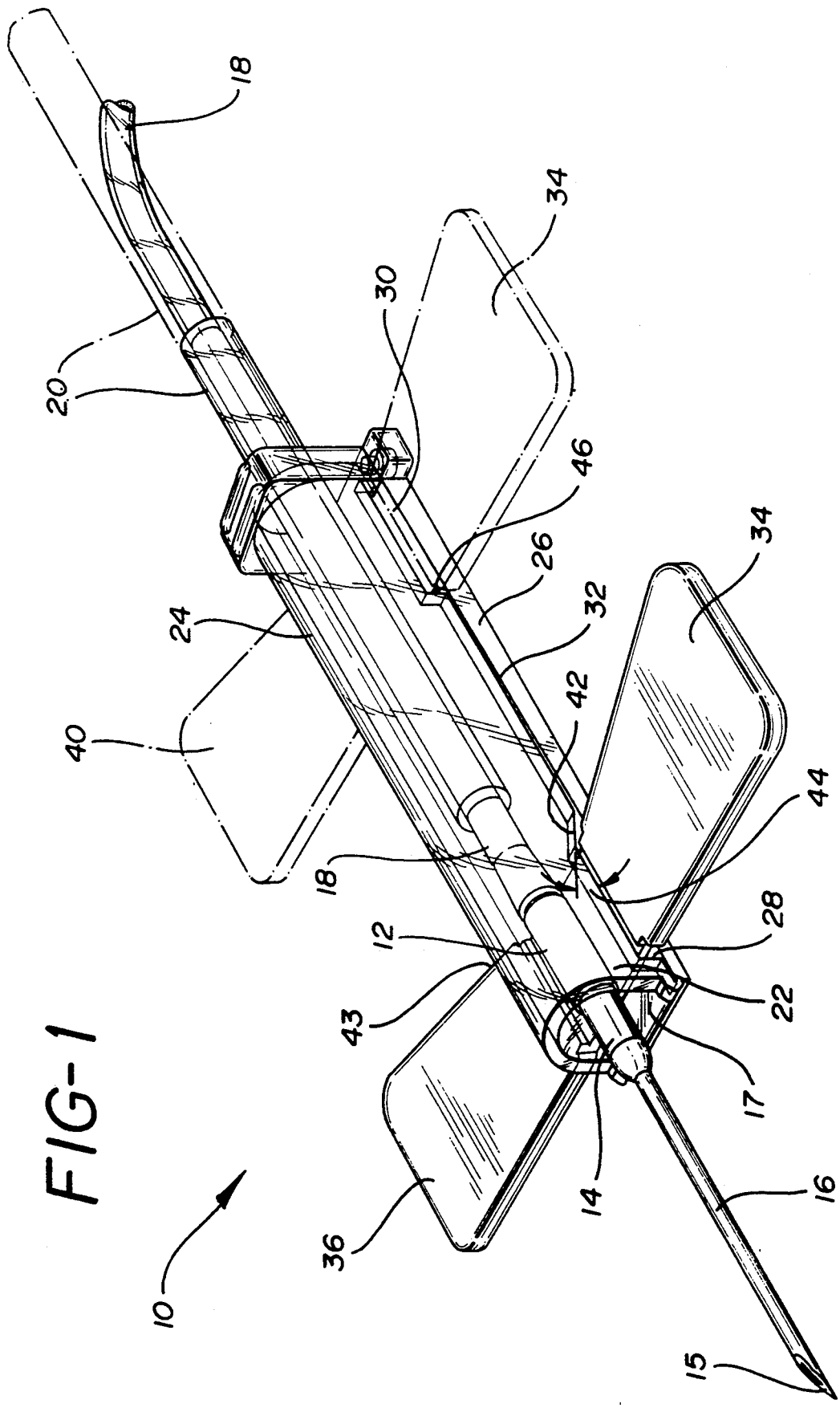
FIG. 1 is a perspective view partially broken away of the assembly of the invention, and showing the position of the needle body, the needle and the wings in a forward use position, and a rearward locking position, the latter being shown in phantom lines.

Referring to the drawings in which like reference characters refer to like parts throughout the several views thereof, FIG. 1 shows the assembly of the invention designated generally with the reference numeral 10, having a conventional infusion or blood collection needle body 12 with a needle hub 14 extending from the front end thereof and a needle 16 embedded in hub 14. Extending from the rear end of body 12 is a tube 18 which is the conventional tubing utilized to allow the user to manipulate the structure of the invention and to connect it subsequently to supplies of infusion liquids, or for the return of collected blood if the arrangement is being used to collect blood.

The structure may or may not include an extension rod 20 which serves to act as a handle for the user when withdrawing the needle 16 into the shell 22 of the invention. The shell 22 includes an upper arched half 24 and a lower more or less flat half 26, joined together in various ways, as will be discussed below. The two halves have a front groove 28 for accommodating the center portion of wings 34 and a rear locking groove 30 for accommodating the wings in their locked position 40 shown in phantom in FIG. 1.

As can be seen in FIG. 1, the front groove 28 includes a rear beveled surface 42 which may be angled as shown at 44 at 30° from horizontal. This surface 42 serves to cause the rear edge 43 of wings 34 to move into the flexible slot 32 which extends between the front slot 28 and the rear slot or groove 30. The opposed surfaces forming the slot 32 are flexible enough to allow the edge 43 of wings 34 to move into slot 32, and to allow the wings to move from the working position 36 of the wings 34 to the locked or "safe" position 40 once the needle 16 has been used and is contaminated. Rod 20, although not necessary or required, may be used by the user to grasp when causing this movement to the rear from the position 36 to the position 40 of the wings so as not to require grasping the tubing 18.

It should be borne in mind at this point in the description of this invention that the wings shown in FIG. 1 together with the needle body 12, hub 14, needle 16 and tube 18 are the usual structures utilized in the conventional apparatus to which this invention is directed, and referred to in the art as a "butterfly" infusion set. Ordinarily, the structure will include a sleeve covering needle 16 when the structure is packaged for future use in order to maintain the needle 16 sterile and the point thereof sharp.

Referring now to FIG. 2, the structure just described in FIG. 1 is shown from the front end thereof as viewed from the left-hand end in FIG. 1, and shows the conventional blood collection structure with the shield of the invention removed.

FIG. 3 shows a cross-sectional and/or longitudinal sectional view of the needle body 12 having a lumen 50 into which the needle is inserted. The narrowed rear end extension 54 receives the front end of tubing 18 thereover, usually in a frictional grip. It will be understood by practitioners-in-the-art that a heat bond or an adhesive may be used to hold tube 18 on extension 54. FIG. 4 shows this structure with needle 16 inserted in needle hub 14.

FIG. 5 shows a conventional blood infusion set, or butterfly, structure with the wings 34 attached to the body 12. Generally, this will be an integral structure with each wing 34 flexing at a boundary 56. The connectors 58 connecting the wings 34 to the body 12 are of reduced thickness in order to enhance the flexibility of the wings 34 along the fold lines 56, and to facilitate the wings passing through flexible slots 32.

FIG. 6 is a plan view of the shield of the invention in its open position prior to being mounted on a blood infusion and/or collection winged set. This is a preferred structure and includes, for example, a living hinge 60 around which the two parts 24, 26 swing to lock the locking abutments 66 into openings 64 in the end extension 62 of shield half 26. As can be seen in FIG. 6, the portions 42 are the angled surfaces which serve to ease or guide the rear edge 43 of wings 34 into the flexible slot 32 formed on each side of the two parts 24, 26 in their mounted position.

FIG. 7 shows the device of FIG. 6 in a front edge view (the bottom edge is shown as viewed in FIG. 6). Thus, as can be seen, the two halves fold together around living hinge 60 to cause the two surfaces 72, 74 to oppose each other. When the folding takes place, the locking abutments 66 are forced through bores 68 into bores 64 for retaining the two halves together in opposed fashion. This movement causes the shield structure to fold over the winged needle collection assembly as shown in FIG. 1. The folding and locking may be performed manually. However, for mass production purposes it will be performed mechanically. Again, the surface 46 serves to oppose any movement of the wing structure forwardly once it has moved into locking grooves 30. The abutments 70 as shown in FIGS. 7 and 8 serve to provide a gripping surface on the rear end of the sleeve during the movement to cause the wing and needle body structure to move rearwardly for covering the needle 16 by the sleeve 22.

FIG. 8, as can be seen, is a sectional view of the structure just described. While the hinged one-piece structure just described is the most desirable from a user and manufacturing standpoint, it will be understood by practitioners-in-the-art that the shield of the invention may be in two parts with locking structures, such as 64, 66, 68, at both ends to join the two parts together.

It is within the purview of the invention to modify the opposed surfaces of the two parts 24, 26 in minor ways in order to achieve certain different movements of the needle body and wing structure being covered by the shield, in accordance herewith. Thus, referring again to FIGS. 7 and 8, the bottom surface 71 of locking groove 30 may be modified as shown in dotted lines 73 to provide an inclined seat for wings 34. This has the effect of causing point 15 of needle 16 to be deflected away from front opening 17 in the protective sleeve or shield 22 in the permanent locked position of wings 34. Alternatively, a protuberance 81 on surface 75 may have the same effect on the top surface of the wing structure.

Also, inclined surface 42 may be modified as shown at 77 to provide a more directed movement of surface 43 of wings 34 into flexible slot 32.

Finally, surface 74 of sleeve half 26 may be modified, as shown at 75 in order to reposition the needle body slightly, in the use position so that the needle 16 extends from opening 17 at a particular elevation, depending upon user desires.

Figure 9:
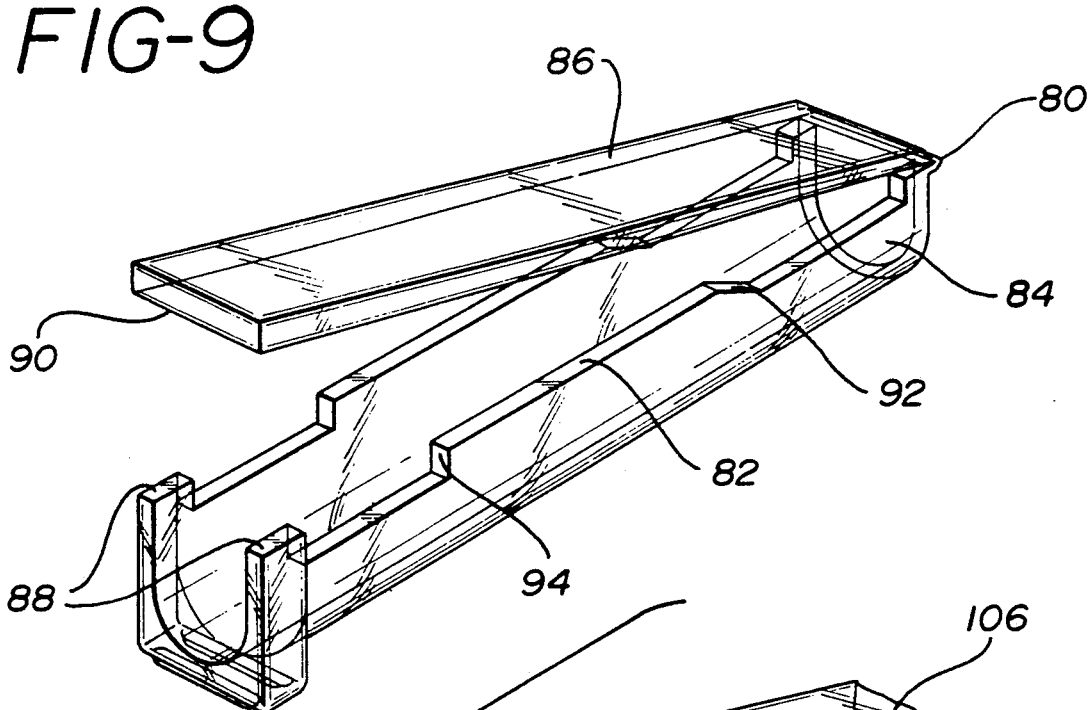
FIGS. 9, 10 and 11 are variations in locking arrangement for the two halves of the shield of the invention.
Figure 10:
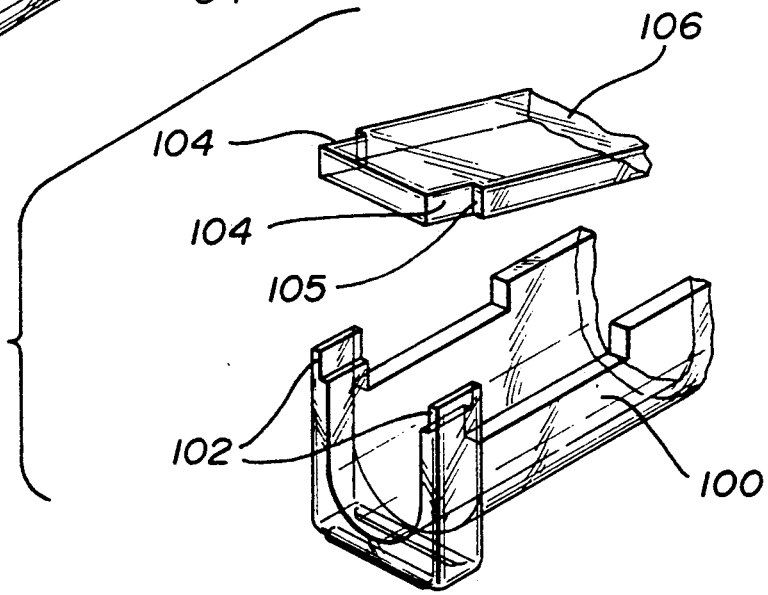
Figure 11:
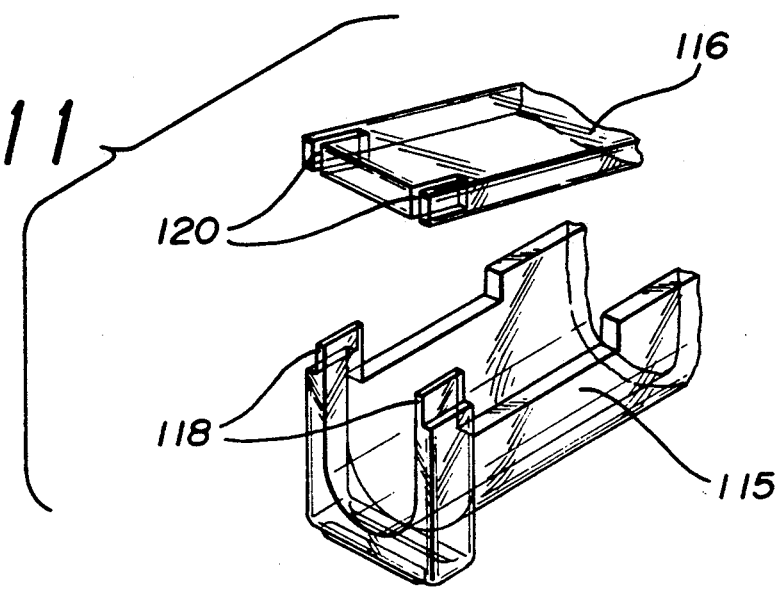

FIGS. 9, 10 and 11 show various alternative arrangements for locking the upper and lower halves of the sleeve 22, rather than the opposed abutment 66 and bores 64, 68 disclosed in the embodiment shown in the above description. For example, in the embodiment of FIG. 9 flat opposed surfaces 88 receive thereon the bottom surface 90 on the flat portion 86 of the shield. The shield has inclined surfaces 92 and perpendicular surfaces 94 which correspond to surfaces 42, 46 in the FIG. 1 embodiment. Likewise, hinge 80 corresponds to hinge 60. With such an arrangement, an adhesive may be used for joining the opposed surfaces together. In this connection, surface 82 also receives an adhesive. Alternatively, as will be understood by practitioners-in-the-art heat welding may take place in order to join these opposed thermoplastic parts together. Thus, as shown in FIG. 9, the upper half 84 of the shield is joined to the lower half 86 by one of these arrangements.

Again, FIG. 10 shows a further arrangement in which the flat portion 106 of a shield may be joined to the upper portion 100 through the opposed surfaces 102, 104, and 105. These surfaces may be joined by selecting an adhesive or they may be heat welded, for example. Finally, as shown in FIG. 11, the flat portion 116 of a shield may include grooves 120 for receiving abutments 118 on the opposed portion 115 of a shield. Again, the opposed surfaces being joined together may be adhered to each other by an adhesive or heat welding, for example. As will be understood by practitioners-in-the-art of formulating thermo-plastic products of the kind discussed herein, other configurations of opposing interlocking surfaces may be utilized.

Thus, as will be appreciated from the above, there is provided in accordance with this invention a conventional I.V. infusion set or blood collection set modified to provide protection for the user by incorporating a shield which may be moved permanently over the contaminated needle once the set has been used, and in a simple easily manipulated manner. Moreover, the shield is comprised of a relatively inexpensive material with very little involved structure.

Thus, the conventional I.V. infusion set, for example, can be modified relatively inexpensively and in an uncomplicated way to provide a throw-away structure. The assembly is comprised of one or two moldable parts which can be mass produced as will be understood, from a variety of materials including, for example, polyethylene, polyvinyl chloride, polystyrene, certain metals or polypropylene. Materials will be selected which will provide the proper covering and support for the structure of the invention in its use, but which will provide also a degree of resiliency for the purposes of providing the cooperative movement relative to the cooperating abutments of the assembly.

While the forms of apparatus herein described constitute preferred embodiments of the invention, it is to be understood that the invention is not limited to these precise forms of apparatus, and that changes may be made therein without departing from the scope of the invention which is defined in the appended claims. For example, the configuration of the two halves of the shield of the invention may be modified to a degree so long as they provide the cooperating forward use lock surfaces, the rearward finally locked surface format, together with the cooperating resilient flexible slot which accommodates the movement of the wings from the forward use position to the rear locked position. Also, as discussed in more detail above, the two parts may be joined together with a living hinge or they may be separately joined with the variety of cooperating front and back abutments for joining the two surfaces together.

What is claimed is:

1. A permanent automatic locking shield for mounting on a conventional winged I.V. infusion set comprising (a) a first elongated shield part;
(b) a second elongated shield part;
(c) means for joining said first, and second shield parts together over a conventional winged I.V. infusion set positioned in and protected by said joined shield parts;
(d) said first shield part being substantially flat for receiving an said I.V. infusion set positioned in said joined shield parts and in sliding engagement for moving said I.V. infusion set and the associated wings therefor positioned in said joined shield parts from a first non-locking use position of a needle of said I.V. set positioned therein and wherein the wings of that set lay to a second permanently locked position therefor;
(e) said second shield part having curved walls for forming a U-shaped chamber with said first shield part, said U-shaped chamber for receiving said I.V. infusion set therein;
(f) said U-shaped chamber having a first end through which the needle of said I.V. infusion set positioned therein extends for use, and a second end through which a tube of said I.V. infusion set positioned therein extends;
(g) a first pair of opposed grooves, in said U-shaped chamber through which the wings of said I.V. infusion set positioned therein extend, one each of said first pair positioned on each side of said locking shield adjacent said first end to form said first non-locking use position of the needle of said I.V. infusion set positioned therein;
(h) a second pair of opposed grooves in said U-shaped chamber spaced from said first pair, with one each of said second pair positioned on each side of said locking shield adjacent said second end to form said permanently locked position for the wings of said I.V. infusion set positioned therein;
(i) a pair of flexible slots one each positioned on each side of said U-shaped chamber, each slot extending from the said respective first non-locking use position groove to the said permanently locked position groove for accommodating the wings of an I.V. infusion set positioned therein moving from said first non-locking use position with the needle of said I.V. infusion set extended for use to said second permanently locked position with the wings of said I.V. infusion set positioned therein; and
(j) a front wall forming each of said permanent locking grooves being perpendicular to the longitudinal axis of said U-shaped chamber;
(k) whereby once the wings of said I.V. infusion set positioned therein move into said second permanently locked position, the said perpendicular front walls prevent movement permanently of the wings forwardly out of said second permanently locked position grooves.

2. The permanent automatic locking shield of claim 1, in which
   (a) said first and second shield parts are a single piece joined at one end by a living hinge.

3. The permanent automatic locking shield of claim 2, in which
   (a) the end of said first and second shield parts opposite said living hinge include cooperating permanent locking abutments on said first part and cooperating permanent locking bores on said second part; and
   (b) said locking bores for receiving said locking abutments when said first and second shield parts are moved adjacent to each other around said living hinge.

4. The permanent automatic locking shield of claim 1, in which
   (a) the bottom surface of said permanent locking grooves are angled from the longitudinal axis of said shield downwardly from said first end of said U-shaped chamber to said second end.

5. The permanent automatic locking shield of claim 1, in which,
   (a) the rear end edge of said first pair of grooves forming said first non-locking use position is angled toward said flexible slots to ease the movement of said wings passing therethrough into said flexible slots.

6. The permanent automatic locking shield of claim 1, in which
   (a) a protuberance on the top surface of each of said permanent locking grooves for engaging and tilting the wings of said I.V. infusion set positioned therein.

7. A permanent automatic locking shield for mounting on a conventional winged I.V. infusion set comprising
   (a) a first elongated shield part;
   (b) a second elongated shield part;
   (c) means for joining said first and second shield parts together over a conventional winged I.V. infusion set positioned in and protected by said joined shield parts;
   (d) said first shield part being substantially flat for receiving said I.V. infusion set positioned in said joined shield parts and in sliding engagement for moving said I.V. infusion set and the associated wings therefore positioned in said joined shield parts from a first non-locking use position of a needle of said I.V. set positioned therein and wherein the wings of the set lay to a second permanently locked position therefor;
   (e) said second shield part having curved walls for forming a chamber with said first shield part, said chamber for receiving said I.V. infusion set therein;
   (f) said chamber having a first end through which the needle of said I.V. infusion set positioned therein extends for use, and a second end through which a tube of said I.V. infusion set positioned therein extends;
   (g) a first pair of opposed grooves in said chamber through which the wings of said I.V. infusion set positioned therein extend, one each of said first pair positioned on each side of said locking shield adjacent said first end to form said first non-locking use position of the needle of said I.V. infusion set positioned therein;
   (h) a second pair of opposed grooves in said chamber spaced from said first pair, with one each of said second pair positioned on each side of said locking shield adjacent said second end to form said permanently locked position for the wings of said I.V. infusion set positioned therein;
   (i) a pair of flexible slots one each positioned on each side of said chamber, each slot extending from the said respective first non-locking use position groove to the said permanently locked position groove for accommodating the wings of said I.V. infusion set positioned therein moving from said first non-locking use position with the needle of said I.V. infusion set extended for use to said second permanently locked position with the wings of said I.V. infusion set positioned therein; and
   (j) a front wall forming each of said permanent locking grooves being perpendicular to the longitudinal axis of said chamber;
   (k) whereby once the wings of said I.V. infusion set positioned therein move into said second permanently locked position, the said perpendicular front walls prevent movement permanently of the wings forwardly out of said second permanently locked position grooves.

* * * * *